United States Patent [19]
Aqui

[11] Patent Number: 5,773,841
[45] Date of Patent: Jun. 30, 1998

[54] SELF ALIGNING VACUUM SEAL ASSEMBLY

[75] Inventor: Derek Aqui, San Jose, Calif.

[73] Assignee: High Yield Technology, Inc., Sunnyvale, Calif.

[21] Appl. No.: 372,257

[22] Filed: Jan. 13, 1995

[51] Int. Cl.$^6$ .................................................. G01N 21/49
[52] U.S. Cl. ........................... 250/573; 356/436; 359/513
[58] Field of Search .......................... 359/513; 250/573; 356/338, 343, 436, 437

[56] References Cited

U.S. PATENT DOCUMENTS

| 3,194,364 | 7/1965 | Kolm ................................... 359/513 X |
| 4,547,673 | 10/1985 | Larsen et al. ........................ 250/573 X |
| 4,643,573 | 2/1987 | McLachlan et al. .................... 356/338 |
| 4,986,636 | 1/1991 | Contzen et al. ..................... 359/513 X |
| 5,305,145 | 4/1994 | Tanaka ..................................... 359/513 |

FOREIGN PATENT DOCUMENTS

| 209070 | 5/1960 | Austria ................................... 359/513 |
| 2003295 | 10/1970 | Germany ................................. 359/513 |

Primary Examiner—Joseph M. Gorski
Attorney, Agent, or Firm—Skjerven, Morrill, MacPherson, Franklin & Friel; Edward C. Kwok

[57] ABSTRACT

A system and a method provide a vacuum seal to be used when mounting an optical device onto a process chamber or a pump line removing exhaust gas from a process chamber. The system of the present invention includes: (a) a threaded nipple, having an internal mating surface and a threaded external surface, that is attached to the process chamber or to the pump line; (b) an internally threaded coupling, provided for accommodating the optical device, that is screwed onto the threaded external surface of the nipple, and having internally a first mating surface touching the internal mating surface of the nipple and a second mating surface; (c) a window placed on the second mating surface of the coupling; (d) means for creating a vacuum seal, e.g. an elastomer O-ring, between the first mating surface of the coupling and the mating surface of the nipple; and (e) means for creating a vacuum seal, e.g. an elastomer O-ring, between the second mating surface of the coupling and the mating surface of the window. In one embodiment, an externally threaded retaining ring located adjacent to the window is screwed into the coupling until the second mating surface of the coupling and the mating surface of the window touch.

9 Claims, 5 Drawing Sheets

5,773,841

SELF ALIGNING VACUUM SEAL ASSEMBLY

BACKGROUND OF THE INVENTION

1. Field of the Invention

This invention relates to a vacuum sealing system and in particular to a sealing system for mounting an optical assembly onto a process chamber or a pump line removing exhaust gas from a process chamber where proper alignment and small size of the optical assembly are critical.

2. Description of the Prior Art

During the processing of semiconductor wafers and the manufacture of integrated circuits, various process gases, such as BCl$_3$ (boron trichloride), for example, are used along with various carrier gases, such as Argon. To ensure that no contaminants are introduced, the process chamber must typically be evacuated to a pressure of a few millitorr. In addition, the process chamber must also be able to contain the process gases, which are often toxic, to prevent such gases from leaking outside of the process chamber. The various components attached to the process chamber, such as vacuum pumps, isolation valves, particle sensors etc. must be properly sealed so that vacuum integrity is maintained.

Various prior art devices have been used to provide a vacuum seal. One such apparatus 100 is shown in FIG. 1. This is an industry standard seal, commonly called "Kwik Flange" or "KF", manufactured by Varian of Lexington, Mass. as well as MDC Vacuum Products Corporation of Hayward, Calif. and several others. A flange 10 is attached to the process chamber 15 (not shown) by means of a continuous weld. An identical flange 11 is similarly attached to the optical apparatus 16 (not shown) to be mounted. A centering ring 12 is used to position an elastomer O ring 13 between the faces of the two flanges. A hinged clamp 14 is then used to compress the two flanges together by means of the beveled outer faces 17 and 18 of the flanges. The pressure of hinged clamp 14 compresses 0-ring 13 between flanges 10 and 11 to provide the vacuum seal. When applied to an optical device such as particle sensor 16, this arrangement of apparatus 100 is characterized by a number of problems. One problem is overall size. The final outer diameter of clamp 14 may be twice as large as the diameter of the optical assembly to be mounted. In addition, clearance must also be provided for installing and removing clamp 14. The clearance dimensions available at any given piece of process equipment in which the optical assembly is to be installed are often difficult to determine without actually attempting installation. Another problem is the orientation of the optical device. Ideally, axis 19 of the optical device should be perpendicular to the flange face. However, uneven compression or relaxation of O-ring 13 over time may cause optical axis 19 to tilt. This tilting of optical axis 19 is especially undesirable for a particle sensor which utilizes a laser beam. A common requirement for proper installation of such a particle sensor is the ability to rotationally align the sensor (and hence the beam), while maintaining the alignment of the optical axis, without breaking the vacuum seal.

Another prior art sealing device 200 is shown in FIG. 2. This is another industry standard commonly called "Conflat" or "CF", manufactured by Varian and others. A metal gasket 15, is compressed between two flanges 16 & 17, using two or more bolts 18. The conical knife edge 19 on each flange causes cold flow of the gasket material to provide the vacuum seal. The arrangement of FIG. 2 has similar drawbacks as the arrangement of FIG. 1. For example, the overall diameter of device 200 may be twice as large as the optical assembly to be mounted, and clearance must also be provided for installing and removing bolts 18. Uneven pressure of bolts 18 may cause the optical axis to tilt, as may further cold flow of gasket 15 after installation.

Other variations of sealing devices exist, with similar drawbacks.

Another problem associated with the above and similar prior art devices relates to the ease of providing heat to the sealing device. Such heating is often desirable and can be achieved using a known technique, commonly used in pump lines of process equipment to prevent deposition of material carried in the process gases. Ease of providing heat to the sealing device becomes especially important when an optical interface is incorporated into the sealing device, since deposition on the optical interface can severely degrade optical performance. The irregular shapes of all of the above prior art devices do not lend themselves to simple heating solutions.

SUMMARY OF THE INVENTION

In accordance with the present invention, a vacuum sealing system and method for mounting an optical device onto a process chamber or alternatively onto a pump line removing exhaust gas from a process chamber are provided. The system of the present invention comprises: (a) a nipple, having an internal mating surface and a threaded external surface, that is attached to the process chamber or alternatively to a pump line removing exhaust gas from a process chamber; (b) an internally threaded coupling, provided for accommodating the optical device, that is screwed onto the threaded external surface of the nipple, and having internally a first mating surface touching the internal mating surface of the nipple and a second mating surface; (c) a window placed on the second mating surface of the coupling; (d) means for creating a vacuum seal between the first mating surface of the coupling and the mating surface of the nipple; and (e) means for creating a vacuum seal between the second mating surface of the coupling and the mating surface of the window.

In one embodiment of the present invention, the means for creating a vacuum seal between the first mating surface of the coupling and the mating surface of the nipple comprises an elastomer O-ring that is inserted on the mating surface of the nipple and located between the first mating surface of the coupling and the mating surface of the nipple.

In another embodiment of the present invention, the means for creating a vacuum seal between the second mating surface of the coupling and the mating surface of the window comprises: an elastomer O-ring inserted on the second mating surface of the coupling and located between the second mating surface of the coupling and the mating surface of the window; and an externally threaded retaining ring located adjacent to the window and screwed into the coupling until the second mating surface of the coupling and the mating surface of the window touch.

According to the invention, any relaxation of the elastomer O-rings will not affect the orientation of the optical device, since the mating surfaces are controlled to be perpendicular to the optical axis. Furthermore, since the outer surface of the coupling is a regular cylinder, localized heating of the window is easily accomplished using a clamp type heater collar and a cartridge heater. In addition, given that the internal threaded diameter is nearly equal to the external diameter the design minimizes the overall diameter of the sealing system. As a further advantage of the present invention, the optical assembly can be rotationally aligned or even removed completely without breaking the vacuum seal. Finally, clearance dimensions are highly predictable since no external clamps or bolts are necessary.

DETAILED DESCRIPTION OF THE PREFERRED EMBODIMENTS

Figure 4:
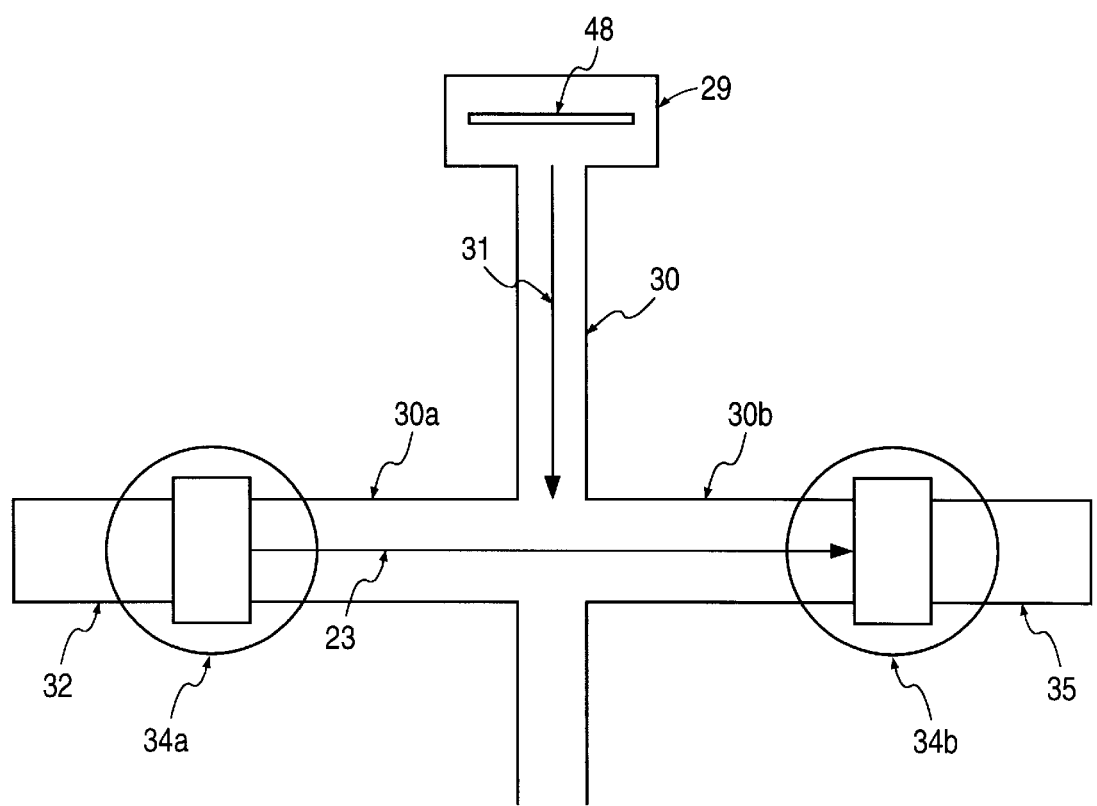
FIG. 4 shows the mounting of a laser source and a laser detector onto a pump line removing exhaust gas from a process chamber, using a vacuum sealing system in accordance with the present invention.

One use for the vacuum sealing system of the present invention is illustrated in FIG. 4. A pump line 30 removes exhaust gas from a process chamber 29 used to process a wafer 48 for the manufacture of an integrated circuit. A laser source 32 is mounted onto a side extension 30a of pump line 30 through a vacuum sealing system 34a in accordance with this invention. A laser detector 35 is mounted onto a side extension 30b of pump line 30 through a vacuum sealing system 34b in accordance with this invention. A laser beam 33 travels from laser source 32 to laser detector 35, across an exhaust gas flow 31.

Figure 5:
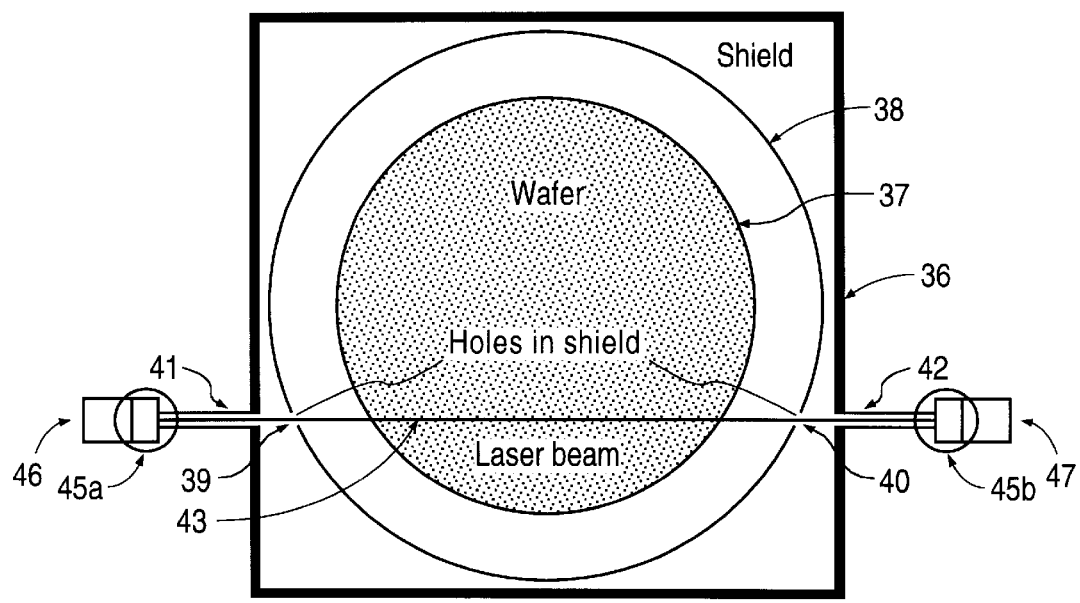
FIG. 5 shows the mounting of a laser source and a laser detector onto tubular extensions of a process chamber, using a vacuum sealing system in accordance with the present invention.

Another use for the vacuum sealing system of the present invention is illustrated in FIG. 5. A processing chamber 36 for the manufacture of integrated circuits is used to process a wafer 37. Wafer 37 is surrounded by a shield 38 which confines the gases produced during the processing of wafer 37. A laser source 46 is mounted onto a tubular extension 41 of process chamber 36 through a vacuum sealing system 45a in accordance with this invention. A laser detector 47 is mounted onto a tubular extension 42 of process chamber 36 through a vacuum sealing system 45b in accordance with this invention. A laser beam 43 travels across process chamber 36 from laser source 46 to laser detector 47 through holes 39 and 40 in shield 38.

Figure 1:
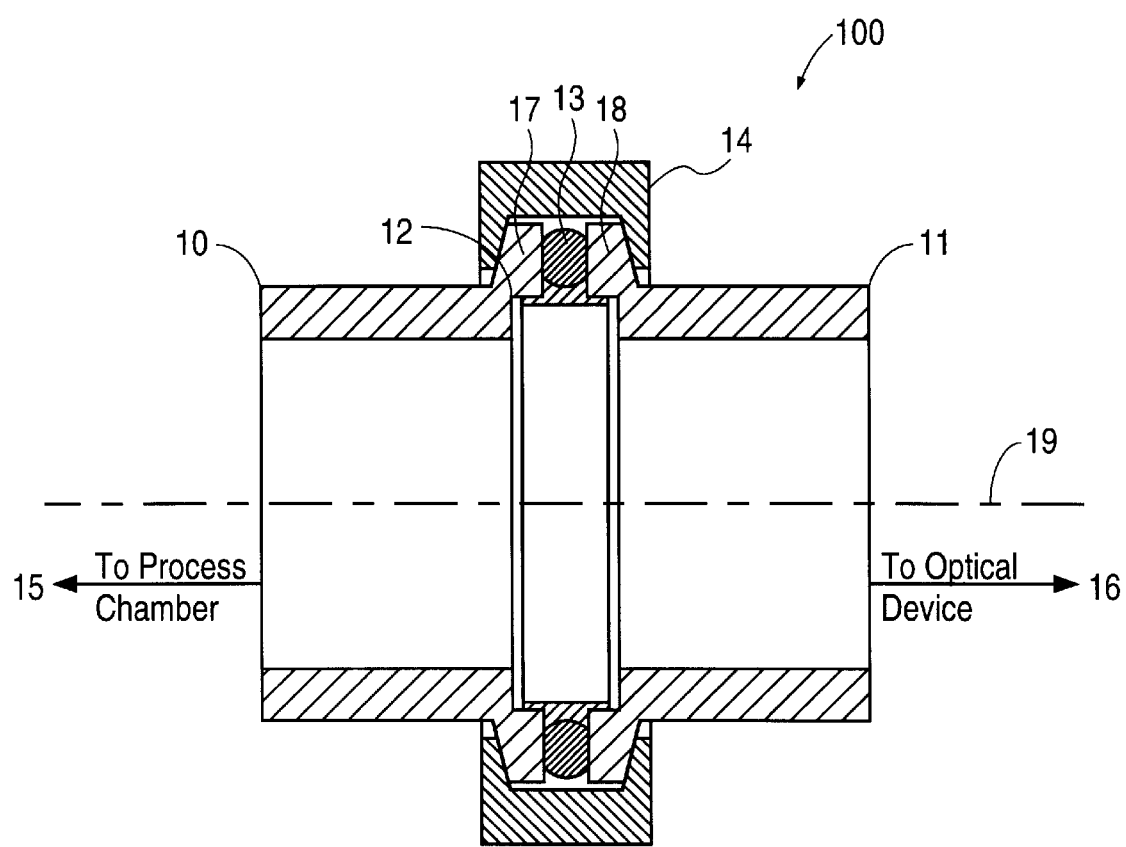
FIG. 1 shows a conventional system 100 in accordance with the prior art, commonly known as "Kwik Flange" or "KF", for providing a vacuum seal when mounting an optical apparatus onto a process chamber.
Figure 2:
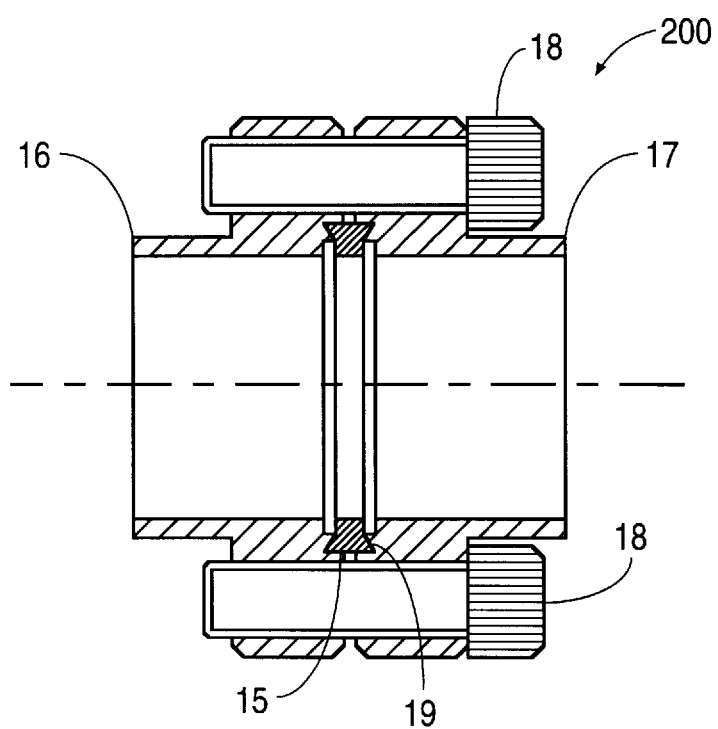
FIG. 2 shows a conventional system 200 in accordance with the prior art, commonly known as "Conflat" or "CF", for providing a vacuum seal when mounting an optical apparatus onto a process chamber.
Figure 3:
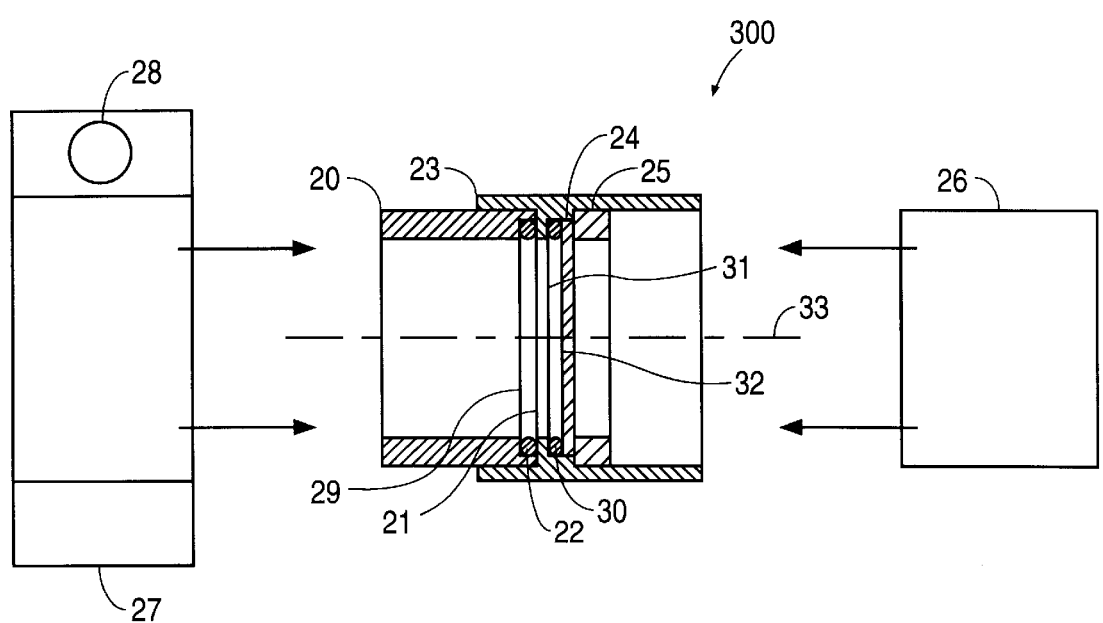
FIG. 3 shows a system 300 for providing a vacuum seal when mounting an optical device onto a process chamber or a pump line removing exhaust gas from a process chamber, in accordance with the present invention.

A view of a vacuum sealing system 300, which is representative of vacuum sealing systems 34a and 34b of FIG. 4 and vacuum sealing systems 45a and 45b of FIG. 5, in accordance with this invention is illustrated in FIG. 3. An externally threaded nipple 20 provided at, for example, a fine 32 threads per inch, is attached to the process chamber (or to a pump line connected to the process chamber) either by a continuous weld or machined directly out of the chamber wall (or the wall of the pump line). An internally threaded coupling 23 is screwed onto nipple 20. In this embodiment, coupling 23 and nipple 20 have mating surfaces 21 and 29, respectively, which are controlled, when properly engaged, to be perpendicular to the optical axis 33 of the optical assembly 26 to within 0.002 inches. In this assembly, an elastomer O-ring 22 is inserted into the counterbore in nipple 20, and coupling 23 is then screwed onto nipple 20 until mating surfaces 21 and 29 touch. The proper engagement of nipple 20 and coupling 23 compresses O-ring 22, thereby providing a vacuum seal between nipple 20 and coupling 23.

Another O-ring 30 and a window 24 are inserted into the counterbore at the back of coupling 23. An externally threaded retaining ring 25, typically of the same thread as nipple 20, is then screwed into the back of coupling 23 until the respective mating surfaces 31 and 32 of coupling 23 and window 24 touch. The proper engagement of coupling 23, window 24 and retaining ring 25 compresses O-ring 30, thereby providing a vacuum seal between window 24 and coupling 23. The optical assembly 26 is then screwed onto the back of coupling 23. In one embodiment, localized heating of window 24 is easily accomplished using a clamp type heater collar 27 and a cartridge heater 28, which are to be positioned over and around coupling 23.

According to this invention, since mating surfaces 21 and 29, as well as mating surfaces 31 and 32, are controlled to be perpendicular to the optical axis 33, any relaxation of elastomer O-rings 22 and 30 will not affect the orientation of optical axis 33. Furthermore, since the outer surface of coupling 23 is a regular cylinder, localized heating of the window is easily accomplished using clamp type heater collar 27 and cartridge heater 28. Since the external diameter of coupling 23 is only slightly greater than the internal threaded diameter of coupling 23, the design minimizes the overall diameter of sealing system 300. Furthermore, optical assembly 26 can be rotationally aligned or even removed completely without breaking the vacuum seal. Also, clearance dimensions are highly predictable since no installations of external clamps or bolts are necessary.

The detailed description above is provided to illustrate the specific embodiments of the present invention and is not intended to be limiting of the present invention. Numerous modifications and variations within the scope of the present invention is possible. The present invention is defined by the following claims.

What is claimed is:

1. A system for providing a vacuum sealed installation of an optical device for use with a process chamber, said system comprising:

a nipple connected to said process chamber, said nipple having a longitudinal axis, an internal mating surface extending perpendicular to said longitudinal axis, and a threaded external surface;

an annular coupling having a longitudinal axis, first and second internal mating surfaces extending perpendicular to said longitudinal axis, a threaded internal surface, and a portion for accommodating an optical device wherein said threaded external surface is threadably engaged with said threaded internal surface such that said first internal mating surface faces said internal mating surface of said nipple, and said second internal mating surface faces away from said mating surface of said nipple, with said first internal mating surface located longitudinally between said second internal mating surface and said internal mating surface of said nipple;

a window, positioned inside said internally threaded coupling, having a mating surface facing said second internal mating surface, with said second internal mating surface located longitudinally between said first internal mating surface and said window;

a first vacuum seal provided between said first mating surface and said mating surface of said nipple; and a second vacuum seal provided between said second mating surface and said mating surface of said window.

2. The system as in claim 1, wherein said first vacuum seal comprises a sealing device that is held in place by said first mating surface urging said sealing device against said mating surface of said nipple.

3. The system as in claim 1, wherein said second vacuum seal comprises:

a sealing device; and an externally threaded retaining ring, located between said window and said optical device, and threadably engaging said internally threaded coupling, such that said externally threaded retaining ring hold said seal device in place by urging said sealing device against said window.

4. The system as in claim 3, wherein said sealing device is an elastomer O-ring.

5. The system as in claim 3, wherein said sealing device is a gasket composed of a malleable metal, such as copper.

6. The system as in claim 2, wherein said sealing device is an elastomer O-ring.

7. The system as in claim 2, wherein said sealing device is a gasket composed of a malleable metal.

8. The system as in claim 1, wherein said nipple is attached to said process chamber by a continuous weld.

9. The system as in claim 1, wherein said nipple is machined directly out of a wall of said process chamber.

* * * * *